(12) United States Patent
Moussou et al.

(10) Patent No.: US 8,247,447 B2
(45) Date of Patent: Aug. 21, 2012

(54) USE OF DERIVATIVES OF 4-HYDROXYPHENOXY ACETIC ACID

(75) Inventors: Philippe Moussou, Tomblaine (FR); Olga Freis, Seichamps (FR); Andreas Rathjens, Tomblaine (FR)

(73) Assignee: Cognis IP Management GmbH, Duesseldorf (DE)

( * ) Notice: Subject to any disclaimer, the term of this patent is extended or adjusted under 35 U.S.C. 154(b) by 342 days.

(21) Appl. No.: 12/530,342

(22) PCT Filed: Feb. 26, 2008

(86) PCT No.: PCT/EP2008/001491
§ 371 (c)(1),
(2), (4) Date: Sep. 8, 2009

(87) PCT Pub. No.: WO2008/107092
PCT Pub. Date: Sep. 12, 2008

(65) Prior Publication Data
US 2010/0297048 A1      Nov. 25, 2010

(30) Foreign Application Priority Data
Mar. 6, 2007   (EP) .................................... 07004524

(51) Int. Cl.
*A01N 37/10*      (2006.01)

(52) U.S. Cl. ....................................... 514/543; 514/887
(58) Field of Classification Search .................... 424/62
See application file for complete search history.

(56) References Cited

FOREIGN PATENT DOCUMENTS

| EP | 0334595 | 9/1989 |
|---|---|---|
| JP | 07082588 A | * 3/1995 |

OTHER PUBLICATIONS

Database WPI Week 200226; Thomas Scientific, London, GB; AN 2002-199604; XP002447333 & JP 2001 354511 A (Shiseido Co. Ltd) Dec. 25, 2001 abstract, claims, paragraph [0064].
Database WPI Week 198847; Thomas Scientific, London, GB; AN 1988-333824; XP002447084 & JP 63 246311 A (Shiseido Co. Ltd) Oct. 13, 1988 abstract.
Database Caplus [Online] Chemical Abstracts Service, Columbus, Ohio, US; Mar. 28, 1995 Oonishi, Takashi et al. Phenoxy alkanoic acids for controlling fragrance or flavor release XP002447094 retrieved from STN.

* cited by examiner

*Primary Examiner* — Patricia A Duffy
*Assistant Examiner* — Dennis J Parad
(74) *Attorney, Agent, or Firm* — DiehlServilla LLC

(57) ABSTRACT

The present invention relates to substances which can be used as cosmetic ingredients, especially for skin whitening and as cosmetic agents against signs of ageing skin. The present invention also relates to the use of such substances for the manufacture of a medicament for the treatment of disorders related to the pigmentation of the skin.

4 Claims, No Drawings

USE OF DERIVATIVES OF 4-HYDROXYPHENOXY ACETIC ACID

CROSS REFERENCE TO RELATED APPLICATIONS

This application is the National Stage entry of PCT/EP2008/001491, filed Feb. 26, 2008, which claims priority to European Patent Application Number EP 07004524.0, filed Mar. 6, 2007, both of which are incorporated herein by reference in their entireties.

FIELD OF THE INVENTION

The present invention relates to substances which can be used as cosmetic ingredients, especially for skin whitening and as cosmetic agents against signs of ageing skin. The present invention also relates to the use of such substances for the manufacture of a medicament for the treatment of disorders related to the pigmentation of the skin.

There is a global market demand for whitening agents in cosmetics to prevent and/or decrease abnormal pigmentations, such as freckles or spots. These are pigmentations due to over exposure to sun. Additionally some dark-skinned individuals prefer lighter skin colour which is regarded as a particular beauty feature.

BACKGROUND OF THE INVENTION 2-(4-Hydroxyphenoxy)alkanoic acids are known as intermediates for herbicides or dyes, e.g. described in EP0334595.

One object of the invention was to provide substances which can be effectively used for the manufacture of or in cosmetic compositions and which are especially suitable as skin whitener and/or as cosmetic agents against the signs of skin ageing. Of special interest was to provide substances which are chemically stable and can thus be easily incorporated into cosmetic compositions. In addition it is desired that these substances do not, or only to a much lower extendt than products known in the market, cause an irritation of the skin onto which it is applied. A further aim of the invention was to provide substances for the manufacture of a medicament for the treatment of disorders related to the pigmentation of the skin.

DETAILED DESCRIPTION OF PREFERRED EMBODIMENTS

The present invention relates to the use of at least one substance of formula (I)

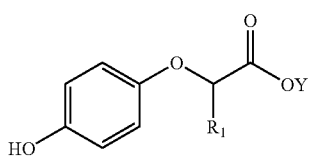

formula (I)

wherein
Y is H, an alkyl or alkenyl group comprising 1 to 8 carbon atoms, a phenyl group, $Na^+$, $K^+$ or $NH_4^+$,
$R_1$ is —H, a linear or branched, saturated or unsaturated alkyl group comprising 1 to 18 carbon atoms, —C(=O)—$R_2$, wherein $R_2$ is a linear or branched, saturated or unsaturated alkyl group comprising 1 to 17 carbon atoms or —$(CH_2)_n$—COOX wherein n is 0 to 17 and wherein X is H, an alkyl or alkenyl group comprising 1 to 8 carbon atoms, a phenyl group, $Na^+$, $K^+$ or $NH_4^+$,
for the manufacture of or in cosmetic and/or topical compositions.

Depending of the substituents Y and R1 the substances according to formula (I) comprise an optically active C atom. In these cases the substance to be used can be either a racemic mixture, the S-enantiomer, the R-enantiomer or any mixture of the enantiomers, which is not a 50:50 mixture (=optically active compound).

Substances According to Formula (I)

Suitable according to the invention are substances according to formula (I)

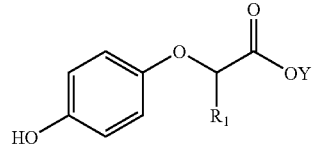

formula (I)

wherein
Y is H, an alkyl or alkenyl group comprising 1 to 8 carbon atoms, a phenyl group, $Na^+$, $K^+$ or $NH_4^+$,
$R_1$ is —H, a linear or branched, saturated or unsaturated alkyl group comprising 1 to 18 carbon atoms, —C(=O)—$R_2$, wherein $R_2$ is a linear or branched, saturated or unsaturated alkyl group comprising 1 to 17 carbon atoms or —$(CH_2)_n$—COOX wherein n is 0 to 17 and wherein X is H, an alkyl or alkenyl group comprising 1 to 8 carbon atoms, a phenyl group, $Na^+$, $K^+$ or $NH_4^+$, Substituent Y Y is selected from the group consisting of H, an alkyl or alkenyl group comprising 1 to 8 carbon atoms, a phenyl group, $Na^+$, $K^+$ and $NH_4^+$. In a preferred embodiment Y is selected from the group consisting of H, and an alkyl or alkenyl group comprising 1 to 8 carbon atoms. The alkyl or alkenyl groups can be linear or branched. Examples of alkyl or alkenyl groups comprising 1 to 8 carbon atoms are Methyl, Ethyl, Propyl-, iso-Propyl [=1-Methylethyl-], Propenyl-, Isobutyl [2-Methylpropyl], sec-Butyl [=1-Methylpropyl], tert-Butyl [1,1-Dimethylethyl], But-2-enyl, But-3-enyl, But-1-enyl, n-Pentyl, 1-Methylbutyl-, 2-Methylbutyl-, 3-Methylbutyl, 1-Ethylpropyl, 1,1-Dimethylpropyl, 1,2-Dimethylpropyl, 2,2-Dimethylpropyl, 1-Pentenyl-, 2-Pentenyl-, 3-Pentenyl-, 4-Pentenyl, Hexyl-, 1-Methylpentyl-, 2-Methylpentyl, 3-Methylpentyl, 4-Methylpentyl, 1-Ethylbutyl-, 2-Ethylbutyl-, 3-Ethylbutyl-, 1-Hexenyl, 2-Hexenyl, 3-Hexenyl, 4-Hexenyl-, 5-Hexenyl, Heptyl, 1-Methylhexyl-, 2-Methylhexyl-, 3-Methylhexyl-, 4-Methylhexyl-, 5-Methylhexyl, 1-Hepentyl, 2-Heptenyl, 3-Heptenyl-, 4-Heptenyl-, 5-Heptenyl, 6-Heptenyl-, n-Octyl, 2-Ethylhexyl-, 1,1,3,3-Tetramethylbutyl-.

In a preferred embodiment Y is selected from the group consisting of H, an alkyl or alkenyl group comprising 1 to 3 carbon atoms, $Na^+$ and $K^+$. In an especially preferred embodiment of the invention Y is H.

Substituent $R_1$ $R_1$ is —H, a linear or branched, saturated or unsaturated alkyl group comprising 1 to 18 carbon atoms, —C(=O)—$R_2$, wherein $R_2$ is a linear or branched, saturated or unsaturated alkyl group comprising 1 to 17 carbon atoms or —$(CH_2)_n$—COOX wherein n is 0 to 17 and wherein X is H, an alkyl or alkenyl group comprising 1 to 8 carbon atoms, a phenyl group, $Na^+$, $K^+$ or $NH_4^+$, Examples of suitable alkyl or alkenyl groups comprising 1 to 18 carbon atoms are Methyl, Ethyl, Propyl-, iso-Propyl [=1-Methylethyl-], Propenyl-, Isobutyl [2-Methylpropyl], sec-Butyl [=1-Methylpropyl], tert-Butyl [1,1-Dimethylethyl], But-2-enyl, But-3-enyl, But-1-enyl, n-Pentyl, 1-Methylbutyl-, 2-Methylbutyl, 3-Methylbutyl, 1-Ethylpropyl, 1,1-Dimethylpropyl, 1,2-Dimethylpropyl, 2,2-Dimethylpropyl, 1-Pentenyl-, 2-Pentenyl-, 3-Pentenyl-, 4-Pentenyl, Hexyl-, 1-Methylpentyl-, 2-Methylpentyl, 3-Methylpentyl, 4-Methylpentyl, 1-Ethylbutyl-, 2-Ethylbutyl-, 3-Ethylbutyl-, 1-Hexenyl, 2-Hexenyl, 3-Hexenyl, 4-Hexenyl-, 5-Hexenyl, Heptyl, 1-Methylhexyl-, 2-Methylhexyl-, 3-Methylhexyl-, 4-Methylhexyl-, 5-Methylhexyl, 1-Hepentyl, 2-Heptenyl, 3-Heptenyl-, 4-Heptenyl-, 5-Heptenyl, 6-Heptenyl-, n-Octyl, 2-Ethylhexyl-, 1,1,3,3-Tetramethylbutyl, Nonyl-, Decyl-, Dodecyl-, Tridecyl-, Tetradecyl-, Pentadecyl-, Hexadecyl-, Heptadecyl-, Octadecyl-.

In one embodiment of the invention $R_1$ is —$(CH_2)_n$—COOX wherein n is 0 to 17 and wherein X is H, an alkyl or alkenyl group comprising 1 to 8 carbon atoms, a phenyl group, $Na^+$, $K^+$ or $NH_4^+$.

In a preferred embodiment of the invention $R_1$ is —$(CH_2)_n$—COOX wherein n is 0 to 17 and wherein X is H.

In a preferred embodiment of the invention $R_1$ is —H, a linear or branched, saturated alkyl group comprising 1 to 12 carbon atoms, preferably 1 to 3 carbon atoms.

In a preferred embodiment of the invention $R_1$ is —$(CH_2)_n$—COOX wherein n is 0, 1 or 2 and X is H.

In a preferred embodiment of the invention $R_1$ is —$CH_3$ and Y is —H.

In a preferred embodiment of the invention $R_1$ is —H and Y is —H.

The following table exemplifies substances according to formula (I) to be used according to the invention:

TABLE 1

| Example No. | $R_1$ | Y | n | X |
|---|---|---|---|---|
| 1a: (4-hydroxyphenoxy)-acetic acid | —H | —H | | |
| 1b | —H | —$CH_3$ | | |
| 1c | —H | —$C_2H_5$ | | |
| 1d | —H | —$C_3H_7$ | | |
| 1e | —H | —COOH | =0 | —H |
| 1f | —H | —$CH_2$—COOH | =1 | —H |
| 1g | —H | —$(CH_2)_2$—COOH | =2 | —H |
| 1h | —H | —$CH_2$—COO—$CH_3$ | =1 | —$CH_3$ |
| 1i | —H | —C(=O)—$CH_3$ | | |
| 1j | —H | —C(=O)—$C_2H_5$ | | |
| 2a: 2-(4-hydroxyphenoxy)-propionic acid | —$CH_3$ | —H | | |
| 2b | —$CH_3$ | —$CH_3$ | | |
| 2c | —$CH_3$ | —$C_2H_5$ | | |
| 2d | —$CH_3$ | —$C_3H_7$ | | |
| 2e | —$CH_3$ | —COOH | =0 | —H |
| 2f | —$CH_3$ | —$CH_2$—COOH | =1 | —H |
| 2g | —$CH_3$ | —$(CH_2)_2$—COOH | =2 | —H |
| 2h | —$CH_3$ | —$CH_2$—COO—$CH_3$ | =1 | —$CH_3$ |
| 2i | —$CH_3$ | —C(=O)—$CH_3$ | | |
| 2j | —$CH_3$ | —C(=O)—$C_2H_5$ | | |
| 3a | —$C_2H_5$ | —H | | |
| 3b | —$C_2H_5$ | —$CH_3$ | | |
| 3c | —$C_2H_5$ | —$C_2H_5$ | | |
| 3d | —$C_2H_5$ | —$C_3H_7$ | | |
| 3e | —$C_2H_5$ | —COOH | =0 | —H |
| 3f | —$C_2H_5$ | —$CH_2$—COOH | =1 | —H |
| 3g | —$C_2H_5$ | —$(CH_2)_2$—COOH | =2 | —H |
| 3h | —$C_2H_5$ | —$CH_2$—COO—$CH_3$ | =1 | —$CH_3$ |
| 3i | —$C_2H_5$ | —C(=O)—$CH_3$ | | |
| 3j | —$C_2H_5$ | —C(=O)—$C_2H_5$ | | |
| 4a | —$C_3H_7$ | —H | | |
| 4b | —$C_3H_7$ | —$CH_3$ | | |
| 4c | —$C_3H_7$ | —$C_2H_5$ | | |
| 4d | —$C_3H_7$ | —$C_3H_7$ | | |
| 4e | —$C_3H_7$ | —COOH | =0 | —H |
| 4f | —$C_3H_7$ | —$CH_2$—COOH | =1 | —H |
| 4g | —$C_3H_7$ | —$(CH_2)_2$—COOH | =2 | —H |
| 4h | —$C_3H_7$ | —$CH_2$—COO—$CH_3$ | =1 | —$CH_3$ |
| 4i | —$C_3H_7$ | —C(=O)—$CH_3$ | | |
| 4j | —$C_3H_7$ | —C(=O)—$C_2H_5$ | | |

The substances according to formula (I) are either commercially available, such as for example 2-(4-hydroxyphenoxy)-propionic acid [CAS N° 67648-61-7], (R)-(+)-2-(4-hydroxyphenoxy)-propionic acid [CAS N° 94050-90-5] or (4-hydroxyphenoxy)-acetic acid [CAS1878-84-8], all from Sigma-Aldrich, or can be obtained by known methods of preparative organic chemistry, or by microbial or enzymatic hydroxylation of related phenoxy-compounds.

Cosmetic Compositions

Cosmetic compositions shall mean any preparation intended to be placed in contact with the various external parts of the human body (epidermis, hair system, nails, lips and external genital organs) or with the teeth and the mucous membranes of the oral cavity with a view exclusively or mainly to cleaning them, perfuming them, changing their appearance and/or correcting body odours and/or protecting them or keeping them in good condition.

The cosmetic compositions according to the invention can for example be in the form of a hair shampoos, hair lotions, foam baths, shower baths, creams, gels, lotions, alcoholic and aqueous/alcoholic solutions, emulsions, wax/fat masses, stick preparations, powders or ointments. These compositions can also comprise, as further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, hydrotropes, solubilizers, preservatives, perfume oils, dyes and the like.

The substance according to formula (I) can be used in cosmetic and/or topical compositions in an amount of 0,0001 to 10 weight-% based on the total weight of the composition, preferably in an amount of 0,001 to 5, especially in an amount of 0,01 to 3 weight-% based on the total weight of the composition.

The present invention also relates to cosmetic and/or topical compositions comprising a substance according to formula (I) and at least one skin-whitening active.

The invention encompasses the finding that substances of formula (I) are advantageously to be used as skin-whitening active. It is to be understood that compositions of the present invention comprise at least one substance according to formula (I) [preferably as a skin-whitener] and at least one (other) skin-whitening active, which is different from a substance according to formula (I). In this preferred embodiment the two actives can act synergistically to provide a highly efficient cosmetic composition.

Skin-whitening Actives

The further skin-whitening active can be chosen from any known skin-whitening agent, e.g. kojic acid, hydroquinone, alpha- and beta-arbutin, other hydroquinone glycosides, deoxyarbutin, ferulic acid, diacetyl-boldine, azelaic acid, octadecenedioic acid, linoleic acid, conjugated linoleic acid, alpha-lipoic acid, glutathione and derivatives, undecylenoyl-phenylalanine, vitamin C and derivatives as magnesium L-ascorbyl-phosphate, niacinamide, 4-n-butyl-resorcinol, alpha- and beta-hydroxy acids, ellagic acid, resveratrol, Morus alba extracts, glabridin and liquorice extracts, imperatorin and isoimperatorin and Angelica dahurica extracts, centaureidin and Yarrow extracts, Bellis perennis extracts, Phyllanthus emblica extracts, water cress extracts, Veratum nigrum extracts, Sophora flavescens extracts, ascomycete-derived melanin-degrading enzyme.

In one embodiment of the invention the further skin-whitening active is at least one plant extract.

In one embodiment of the invention the further skin-whitening active is selected from the group consisting of kojic acid, alpha- and beta-arbutin, other hydroquinone glycosides, deoxyarbutin, ferulic acid, conjugated linoleic acid, vitamin C and derivatives such as magnesium L-ascorbylphosphate, niacinamide, liquorice extracts and combinations thereof.

The substances of formula (I) to be used according to the invention as well as the compositions are especially suitably used for the lightening and/or whitening of skin and/or for the reduction of pigmentation and/or reduction of hyperpigmentation and/or inhibition of melanogenesis.

The invention encompasses the finding that substances of formula (I) as well as the compositions are especially suitably used for the prevention and/or retardation of signs of ageing and/or improving the skin appearance of aged skin, such as for example sallowness, decrease of skin thickness, fine lines, wrinkles, sagging, diminished rate of turnover, abnormal desquamation.

The invention is further directed to the use of a substance according to formula (I) for the manufacture of a medicament for the treatment of a disease connected to a disorder in the pigmentation of the skin.

Such hyperpigmentation diseases are for example chloasma (a hypersecretion of melanin induced by hormonal factors and amplified by the effects of sun exposition), lentigines, solar and senile lentigo, Dubreuilh melanosis, or any form of hypermelanosis or melanocyte dysfunction.

EXAMPLES

Example 1

Substance 2-(4-hydroxyphenoxy)-propionic acid [CAS N° 67648-61-7, racemate] is available from Sigma-Aldrich.

Example 2

Melanogenesis Inhibition Assay

Melanocytes (B16 cell line) were inoculated in standard medium of cell culture with foetal calf serum (FCS). After an incubation of 3 day at 37° C. and CO2=5%, growth medium was exchanged for standard medium with a range of concentrations for each compound to be tested and a control without ingredient. After an incubation of 3 days, the level of melanin was measured by recording the optical density at 475 nm. After washing the cells by a balanced salt, and homogenisation in a solution of 0.1 M NaOH, the number of viable cells was determined by evaluation of the level of cellular proteins (Bradford's method). The results are expressed in % against control (cell culture medium without compound) as a mean on 1 to 3 assays, each in triplicate.

TABLE 2

Rate of cellular proteins & melanin in %/control (mean of assays in triplicate):

| | Dose % (w/v) | Protein level | Melanin level |
|---|---|---|---|
| Control | — | 100 +/− 0 | 100 +/− 0 |
| 2-(4-hydroxyphenoxy)-propionic acid | 0.00003 | 103 | 84 |
| | 0.0001 | 97 | 57 |
| | 0.0003 | 107 | 52 |
| | 0.001 | 104 | 39 |
| | 0.01 | 98 | 37 |

The results demonstrated that tested compound according to formula (I) with Y=H, and $R_1$=Methyl has decreased in a dose dependant manner the rate of melanin synthesis in melanocytes, without any cell toxicity even for doses up to 0.01%.

What is claimed is:

1. A method for inhibiting melanogenesis in the skin of a subject in need thereof, comprising topically applying to the skin a composition, comprising at least one substance of formula (I),

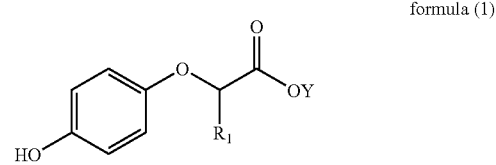

formula (I)

wherein Y is H, C1-C8 alkyl, C2-C8 alkenyl, phenyl, $Na^+$, $K^+$ or $NH^{4+}$, $R_1$ is H, a linear or branched, saturated or unsaturated alkyl group comprising 1 to 18 carbon atoms, —C(=O)—$R_2$, wherein $R_2$ is a linear or branched, saturated or unsaturated alkyl group comprising 1 to 17 carbon atoms, or —$(CH_2)_n$—COOX wherein n is a to 17 and wherein X is H, C1-C8 alkyl, C2-C8 alkenyl, phenyl, $Na^+$, $K^+$ or $NH^{4+}$, in an amount effective to inhibit melanogenesis.

2. The method of claim 1, wherein the compound of formula (I) is present in an amount of from 0.0001 to 10 wt-% based on the total weight of the composition.

3. The method of claim 1, wherein the at least one substance of formula (I) is racemic or optically active.

4. The method of claim 1, wherein the composition further comprises a skin whitening agent.

* * * * *